US009608395B2

(12) United States Patent
Overweg

(10) Patent No.: US 9,608,395 B2
(45) Date of Patent: Mar. 28, 2017

(54) SLIP RING ASSEMBLY

(75) Inventor: Johannes Adrianus Overweg, Uelzen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 879 days.

(21) Appl. No.: 13/991,629

(22) PCT Filed: Dec. 7, 2011

(86) PCT No.: PCT/IB2011/055508
§ 371 (c)(1),
(2), (4) Date: Sep. 30, 2013

(87) PCT Pub. No.: WO2012/077064
PCT Pub. Date: Jun. 14, 2012

(65) Prior Publication Data
US 2014/0043027 A1    Feb. 13, 2014

(30) Foreign Application Priority Data

Dec. 8, 2010  (GB) .................................. 1020796.7
Jun. 14, 2011  (EP) .................................... 11169763

(51) Int. Cl.
*G01V 3/00* (2006.01)
*H01R 39/08* (2006.01)
(Continued)

(52) U.S. Cl.
CPC ........... *H01R 39/08* (2013.01); *A61B 5/0035* (2013.01); *A61B 5/055* (2013.01); *A61B 6/032* (2013.01);
(Continued)

(58) Field of Classification Search
CPC .... H01R 39/08; H01R 2201/12; G01R 33/36; G01R 33/4808; G01R 33/4812;
(Continued)

(56) References Cited

U.S. PATENT DOCUMENTS 4,334,159 A  *  6/1982  Ooki .................... H02K 9/28
                                               310/232
5,208,581 A  *  5/1993  Collins ................. A61B 6/56
                                               310/232
(Continued)

FOREIGN PATENT DOCUMENTS

EP        0743719 A2  *  11/1996  ............. H01R 39/08
GB        780146           7/1957
(Continued)

OTHER PUBLICATIONS

Uchiyama, "Slip Ring", Jan. 12, 1996, JP08-008019A, Machine English Translation by JPO, Claims, Detailed Description, Description of Drawings, Drawings.*

*Primary Examiner* — Susan Lee

(57) ABSTRACT

A medical apparatus (600) including: a magnetic resonance imaging system (602), a medical device (634), and a slip ring assembly (400, 500) for supplying electrical power to the medical device. The slip ring assembly includes: a cylindrical body (100), a rotating member (402) for rotating the medical device, a first cylindrical conductor attached to the cylindrical body, a second cylindrical conductor (108), a first set of conductive elements (112, 712) connected to the second cylindrical conductor; and a brush assembly (406) comprising a first brush (302) and a second brush (304). The first brush is operable to contact the first cylindrical conductor. The second brush is operable to contact the set of conductive elements. The first and second cylindrical conductive elements overlap at least partially. The second cylindrical conductor is connected to the cylindrical body. The first cylindrical conductor and the second cylindrical conductors are electrically isolated.

13 Claims, 7 Drawing Sheets

(51) Int. Cl.
  *A61B 5/055* (2006.01)
  *A61B 6/03* (2006.01)
  *A61B 6/00* (2006.01)
  *G01R 33/48* (2006.01)
  *G01R 33/36* (2006.01)
  *A61N 5/10* (2006.01)
  *A61B 5/00* (2006.01)

(52) U.S. Cl.
  CPC .......... *A61B 6/4417* (2013.01); *A61N 5/1081* (2013.01); *G01R 33/36* (2013.01); *G01R 33/4808* (2013.01); *A61B 6/56* (2013.01); *A61N 2005/1055* (2013.01); *G01R 33/4812* (2013.01); *H01R 2201/12* (2013.01)

(58) Field of Classification Search
  CPC ....... A61B 5/0035; A61B 5/055; A61B 6/032; A61B 6/4417; A61B 6/56; A61N 5/1081; A61N 2005/1055
  USPC .......................................... 324/319; 310/232
  See application file for complete search history.

(56) References Cited

U.S. PATENT DOCUMENTS

| | | | |
|---|---|---|---|
| 5,224,138 A | 6/1993 | Hirao et al. | |
| 5,285,125 A * | 2/1994 | Lang | H01R 39/42 310/232 |
| 6,608,569 B2 * | 8/2003 | Herold | A61B 6/56 340/686.3 |
| 7,131,844 B1 | 11/2006 | Wurr | |
| 7,570,739 B2 * | 8/2009 | Bergfjord | A61N 5/1081 378/193 |
| 7,741,624 B1 * | 6/2010 | Sahadevan | A61N 5/1081 600/427 |
| 8,836,332 B2 * | 9/2014 | Shvartsman | G01R 33/4808 324/319 |
| 2003/0214421 A1 | 11/2003 | Schilling | |
| 2005/0135560 A1 | 6/2005 | Dafni et al. | |
| 2005/0280329 A1 | 12/2005 | Day et al. | |
| 2007/0053486 A1 * | 3/2007 | Zelnik | A61B 6/04 378/20 |
| 2009/0012383 A1 * | 1/2009 | Virtue | A61B 6/032 600/407 |
| 2009/0149735 A1 * | 6/2009 | Fallone | A61N 5/1049 600/411 |
| 2010/0074394 A1 * | 3/2010 | Nakamura | A61B 5/08 378/8 |
| 2010/0312097 A1 * | 12/2010 | Gallant | A61B 5/055 600/411 |
| 2011/0012593 A1 * | 1/2011 | Shvartsman | G01R 33/4808 324/307 |

FOREIGN PATENT DOCUMENTS

| | | | | |
|---|---|---|---|---|
| GB | 2067523 A | | 7/1981 | |
| GB | 2393373 A | | 3/2004 | |
| JP | 03207345 A | | 9/1991 | |
| JP | 03289078 A | * | 12/1991 | |
| JP | 088019 A | | 1/1996 | |
| JP | 08008019 A | * | 1/1996 | |
| JP | 2006074906 A | | 3/2006 | |
| WO | WO 0150578 A1 | * | 7/2001 | ............. H01R 39/08 |

* cited by examiner

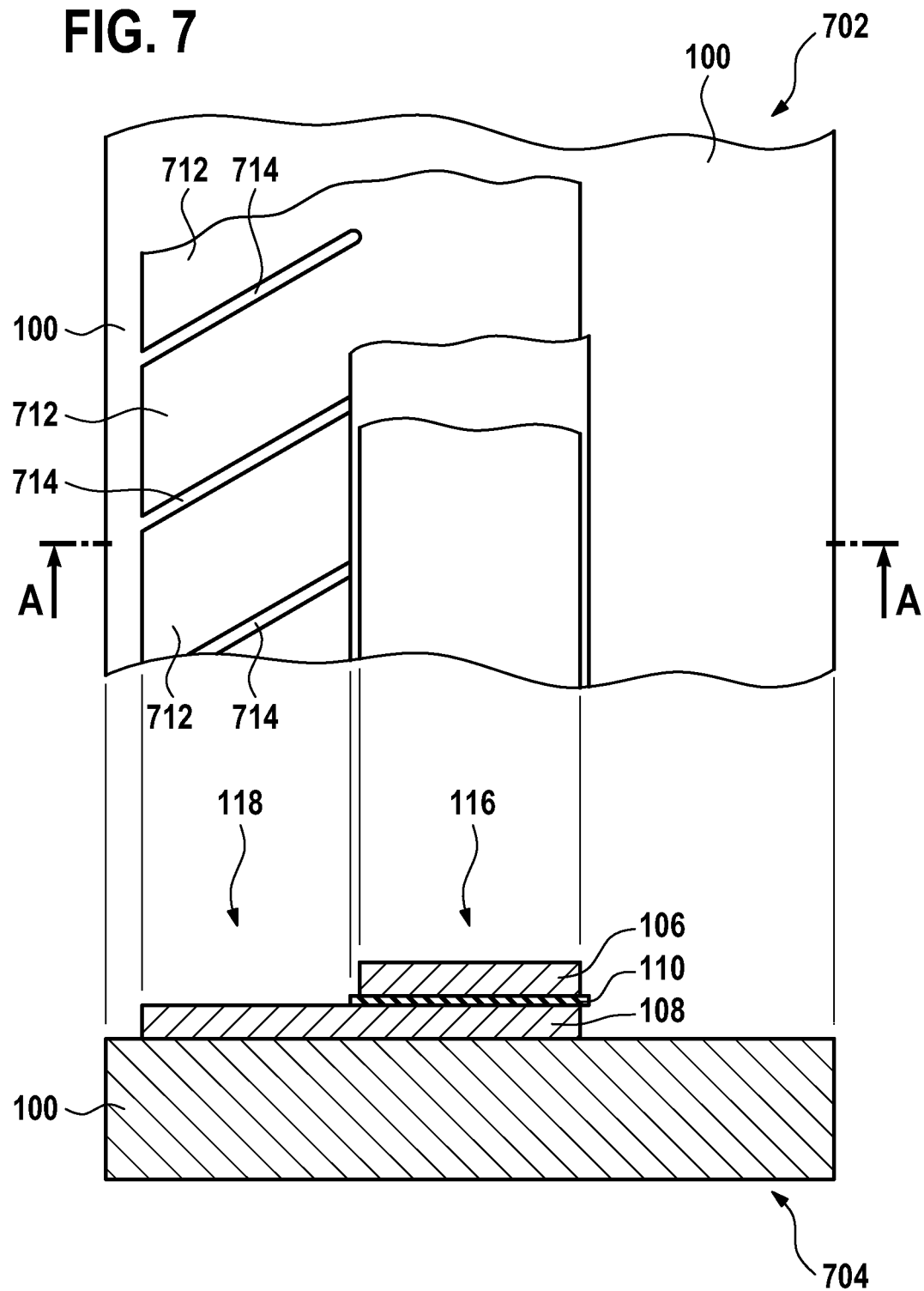

SLIP RING ASSEMBLY

TECHNICAL FIELD

The invention relates to magnetic resonance imaging, in particular to the combination of magnetic resonance imaging with other imaging modalities or with radiation therapy.

BACKGROUND OF THE INVENTION

A static magnetic field is used by Magnetic Resonance Imaging (MRI) scanners to align the nuclear spins of atoms as part of the procedure for producing images within the body of a subject. During an MRI scan, Radio Frequency (RF) pulses generated by a transmitter coil cause perturbations to the local magnetic field, and RF signals emitted by the nuclear spins are detected by a receiver coil. These RF signals are used to construct the MRI images.

Rapidly acquiring magnetic resonance images has been successfully used to guide various modalities of radiation therapy. Magnetic resonance may also be combined with other medical imaging modalities. For some modalities a medical apparatus may be mounted on a rotating gantry.

SUMMARY OF THE INVENTION

The invention relates to a medical apparatus and a slip ring assembly in the independent claims. Embodiments are given in the dependent claims.

For example a radiation source such as a linear accelerator (LINAC) may be placed on the gantry and used to irradiate a subject. Such medical devices may be supplied with electrical power by the use of slip rings. A slip ring as used herein encompasses is a sliding or rotating electrical contact. A difficulty is that if significant amounts of electrical current are supplied to the medical device the currents may produce a magnetic field which is strong enough to affect the measurements made by the magnetic resonance imaging system. Embodiments of the invention may address this and other problems by positioning conductors within a slip ring assembly to reduce magnetic field generated by the slip ring assembly. Embodiments may use cylindrical conductors that at least partially overlap such that the magnetic field that is generated is reduced.

For example, a Slip-Ring assembly, used to supply electric power to a treatment device orbiting an MRI scanner, is shaped such that the magnetic stray field of the currents flowing in the ring are reduced. Such fields would otherwise reduce the MR image quality. In some embodiments, the design can be characterized as a multi-layer structure in which the width of the layers increases from layer to layer. Lateral slits confine the transport currents to the central region of the assembly whereas the brushes picking up the current ride over the slit edges of the conductor layers.

A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network.

'Computer memory' or 'memory' is an example of a computer-readable storage medium. Computer memory is any memory which is directly accessible to a processor. Examples of computer memory include, but are not limited to: RAM memory, registers, and register files.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa.

A 'processor' as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have their instructions performed by multiple processors that may be within the same computing device or which may even be distributed across multiple computing devices.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

In one aspect the invention provides for a medical apparatus comprising a magnetic resonance imaging system for acquiring magnetic resonance data. The magnetic resonance imaging system comprises a magnet. The medical apparatus further comprises a medical device. The medical apparatus further comprises a slip ring assembly operable for supplying electrical power to the medical device. The slip ring assembly comprises a cylindrical body with an axis of symmetry. The slip ring assembly further comprises a rotating member for rotating about the axis of symmetry. The slip ring assembly also rotates about the magnet. The medical device is mounted to the rotating member. In other words the slip ring assembly comprises a rotating member to which the medical device is attached. The medical device is then rotated about the axis of symmetry by the rotating member. The slip ring assembly further comprises a first cylindrical conductor. The first cylindrical conductor is attached to the cylindrical body.

The slip ring assembly further comprises a second cylindrical conductor. The first and second cylindrical conductors overlap at least partially. In some embodiments the first and second cylindrical conductive elements overlap entirely. The second cylindrical conductor is connected to the cylindrical body. The first cylindrical conductor and the second cylindrical conductors are electrically isolated. There may be for instance a layer of insulation material between the first cylindrical conductor and the second cylindrical conductor. The slip ring assembly further comprises a first set of conductive elements. Each of the set of conductive elements is connected to the second cylindrical conductor.

The slip ring assembly further comprises a brush assembly comprising a first brush and a second brush. The first brush is operable to contact the first cylindrical conductor when the rotating member rotates about the axis of symmetry. The second brush is operable to contact the set of conductive elements when the rotating member rotates about the axis of symmetry. This embodiment may be advantageous because the first and second cylindrical conductors at least partially overlap. The conduction of current on the first and second cylindrical conductors will generate a magnetic field which may disturb the magnetic resonance imaging system. However, because the first and second cylindrical conductors overlap the magnetic field generated by each will at least partially cancel. This reduces the effect of supplying electrical power to the medical device. The medical device may for instance be a device which generates or detects radiation and uses a significant amount of electrical current.

The first set of conductive elements may be a set of paths or other conductors which are not connected electrically. They may be connected electrically to the second cylindrical conductor. The brushes contact the first set of conductive elements. Since they are not continuously connected electrical current will not be conducted through the set of conductive elements. This forces the current through the second cylindrical conductor. Since the first and second cylindrical conductors are at least partially overlapping the paths of the currents generate magnetic fields that at least approximately cancel each other.

In another embodiment the set of conductive elements is formed by a first cylindrical contact. The first cylindrical contact is separated into the set of conductive elements by electrically isolating grooves. This embodiment may be advantageous because the cylindrical contact forms a cylindrical band that may be easily brought into electrical contact with the second brush. The electrically isolating grooves cut into the first cylindrical contact divide the cylindrical contact into the set of conductive elements. These grooves prevent current from flowing along or around the first cylindrical contact. This forces the current to flow through the second cylindrical conductor.

In another embodiment the first cylindrical conductor has an axis of symmetry that is identical with the axis of symmetry of the cylindrical body.

In another embodiment the second cylindrical conductor has an axis of symmetry that is identical with the axis of symmetry of the cylindrical body.

In another embodiment the first cylindrical contact has an axis of symmetry that is identical with the axis of symmetry of the cylindrical body.

In another embodiment the electrically isolating grooves are formed at a predetermined angle with respect to a projection of the axis of symmetry onto the first cylindrical contact. This embodiment may be advantageous because the isolating grooves are slanted with respect to the travel of the brushes over the first set of conductive elements. As the brush travels over the conductive elements it may be in contact with more than one conductive element at a particular time. This would mean for instance that there is reduced possibility that electrical contact may be broken briefly as the rotating member rotates.

In another embodiment the isolating grooves form a fishbone pattern.

In another embodiment at least one of the first cylindrical conductor and the second cylindrical conductor comprise an electrically isolating break at a predetermined rotational angle of the rotating member. This embodiment may be particularly advantageous because it forces the current to flow through a particular portion of the first cylindrical conductor and/or the second cylindrical conductor. Without an isolating break there are two parallel paths for the current to flow from the point where the current enters the cylindrical conductor to where the brush makes contact (clockwise and anti-clockwise). If the ratio of clockwise versus anti-clockwise current differs between the first and second cylindrical conductors (for example because of differences in resistance) a net circulating current there is flowing around the entire cylinder. An electrically isolating break in one or both of the first and second cylindrical conductors forces the current to flow along a predefined path. This reduces the size of the current loop between the first and second cylindrical conductors and thereby reduces the magnetic field generated which reduces the effect on the magnetic field of the magnetic resonance imaging system.

In another embodiment the medical apparatus comprises a control system to halt the acquisition of the magnetic resonance data by the magnetic resonance imaging system when the rotating member is within a predetermined angular range of the predetermined rotational angle. For instance what may happen is that as the brushes rotate into the proper position there may be a time when current is not flowing or flowing across both sides of the break. By not acquiring magnetic resonance data when the rotating member is in this position the chances of an artifact in the MRI image due to this break is greatly reduced.

In another embodiment the rotating member comprises the brush assembly. That is to say the brush assembly is attached to the rotating member. As the rotating member rotates around the brush assembly is in contact with a cylindrical body that is fixed.

In another embodiment the rotating member comprises the cylindrical body. In this embodiment the cylindrical body is or is a part of the rotating member. The brushes are held in a fixed position with respect to the cylindrical body as it rotates. This embodiment may be particularly advantageous because the brushes may be placed in a position not accessible to a patient. For instance if the brushes are rotating as opposed to the cylindrical body carbon fragments from the brush assembly may fall down onto the magnetic resonance imaging system.

In another embodiment the medical apparatus further comprises a third cylindrical conductor. The first cylindrical conductor and the third cylindrical conductor overlap at least partially. The third cylindrical conductor is connected to the cylindrical body. The third cylindrical conductor and the second cylindrical conductors are electrically isolated. The third cylindrical conductor and the first cylindrical conductor are electrically isolated. The medical apparatus further comprises as second set of conductive elements. Each of the set of conductive elements is connected to the third cylindrical conductor. The brush assembly comprises a third brush. The third brush is operable to contract the second set of conductive elements when the rotating member rotates about the axis of symmetry. This embodiment is particularly advantageous because three phase power may be supplied to the medical device. The embodiments descriptive of the second cylindrical conductor and/or the first set of conductive elements are also applicable to the third cylindrical conductor and the second set of conductive elements respectively.

In another embodiment the second set of conductive elements is formed by a second cylindrical contact. The second cylindrical contact is separated into the set of conductive elements by the second electrically isolating grooves. The second electrically isolating grooves are formed at a second predetermined angle with respect to a projection of the axis of symmetry onto the second cylindrical contact. The second predetermined angle may be identical with or different from the predetermined angle. The advantage of this embodiment is equivalent with the advantage to the embodiment with the electrically isolating grooves and the first cylindrical contact.

In another embodiment the second cylindrical contact may have an axis of symmetry that is identical with the axis of symmetry of the cylindrical body.

In another embodiment the medical device is an x-ray machine.

In another embodiment the medical device is a linear accelerator or LINAC.

In another embodiment the medical device is charged particle beam optics.

In another embodiment the medical device is a computer tomography system.

In another aspect the invention provides for a slip ring assembly. The slip ring assembly comprises a cylindrical body with an axis of symmetry. The slip ring assembly further comprises a rotating member for rotating about the axis of symmetry. The slip ring assembly further comprises a first cylindrical conductor. The first cylindrical conductor is attached to the cylindrical body. The slip ring assembly further comprises a second cylindrical conductor. The first and second cylindrical conductive elements overlap at least partially. The second cylindrical conductor is connected to the cylindrical body. The first cylindrical conductor and the second cylindrical conductors are electrically isolated. The slip ring assembly further comprises a set of conductive elements. Each of the set of conductive elements is connected to the second cylindrical conductor. The slip ring assembly further comprises a brush assembly comprising a first brush and a second brush. The first brush is configured to contact the first cylindrical conductor when the rotating member rotates about the axis of symmetry. The second brush is configured to contact the set of conductive elements when the rotating member rotates about the axis of symmetry. The second brush does not contact all of the set of conductive elements when the rotating member rotates about the axis of symmetry. The brush may contact one of the set of conductive elements or several of them. The advantages of this slip ring assembly have been previously discussed.

In another embodiment the slip ring assembly further comprises at least one additional cylindrical conductor. The first cylindrical conductive element and the at least one additional cylindrical conductor at least partially overlap. The at least one additional cylindrical conductor is connected to the cylindrical body. The at least one additional cylindrical conductor and the first cylindrical conductor are electrically isolated. The slip ring assembly further comprises at least one additional set of conductive elements. Each of the at least one set of conductive elements is connected to the at least one additional cylindrical conductor. The brush assembly comprises at least one additional brush. The at least one additional brush is operable to contact the at least one additional set of conductive elements when the rotating member rotates about the axis of symmetry. The previously mentioned embodiments which are descriptive of the first cylindrical conductor and/or the first set of conductive elements may be applicable to any number of additional cylindrical conductors. The cylindrical conductors are electrically isolated from each other. The advantages of such a slip ring assembly have been previously discussed.

In another embodiment the rotating member comprises the brush assembly.

In another embodiment the rotating member comprises the cylindrical body.

BRIEF DESCRIPTION OF THE DRAWINGS

In the following preferred embodiments of the invention will be described, by way of example only, and with reference to the drawings in which:

FIG. 7 shows a portion of a cylindrical body according to a further embodiment of the invention.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
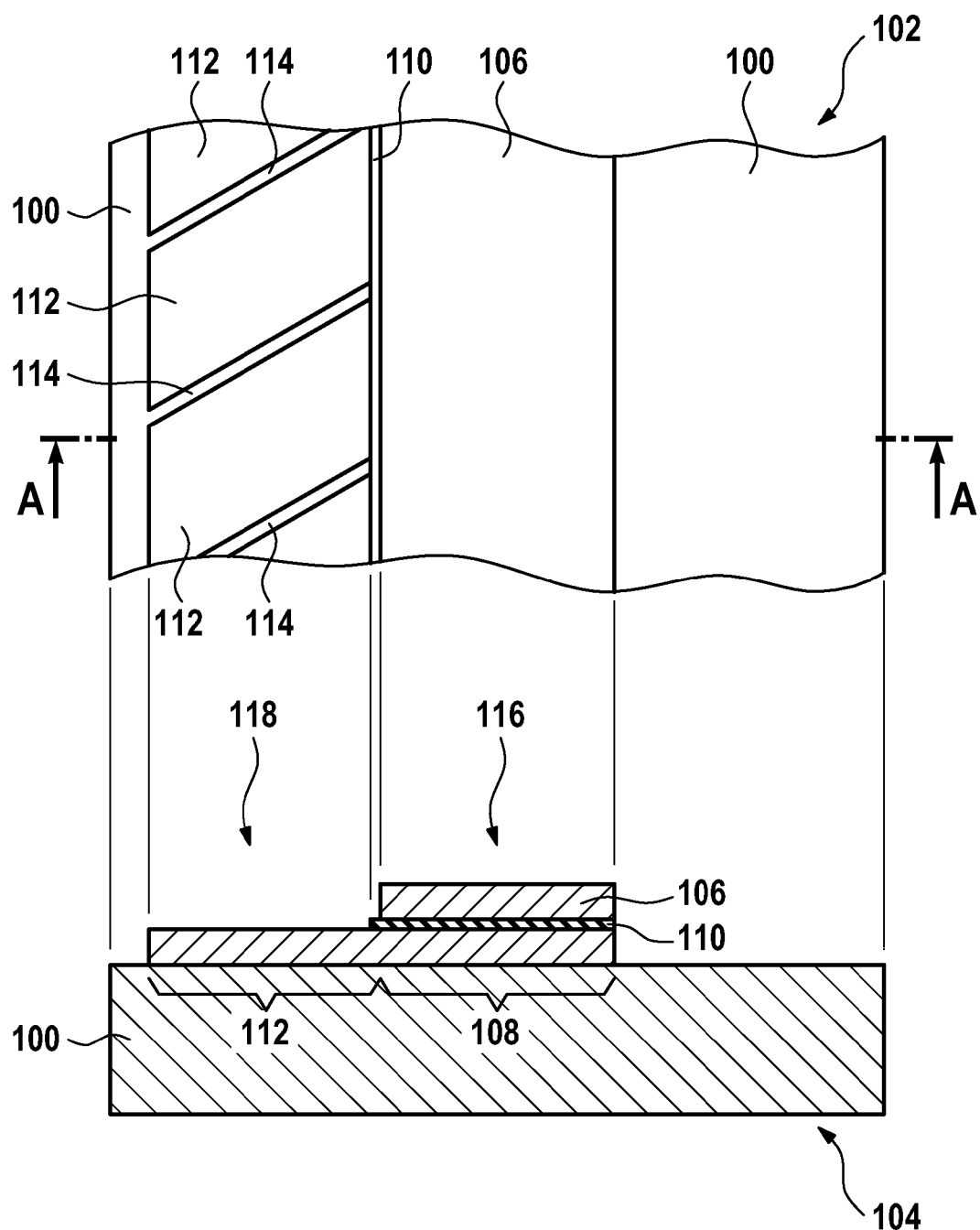
FIG. 1 shows a portion of a cylindrical body according to an embodiment of the invention.

FIG. 1 shows a portion of a cylindrical body 100. View 102 shows a top surface view of the cylindrical body 100. View 104 shows a sectional view along the section line labeled A-A. Visible on both views is the first cylindrical conductor. Below the first cylindrical conductor 106 is the second cylindrical conductor 108. There is an insulating layer 110 separating the first cylindrical conductor 106 from the second cylindrical conductor 108. Looking at the top view to the left of the first cylindrical conductor are several conductive elements 112. The conductive elements 112 form the first set of conductive elements. There is a groove or gap 114 which separates the conductive elements 112. In the side view it can be seen that the conductive elements 112 are each connected to the second cylindrical conductor 108. The surface marked 116 is the surface along which the first brush would contact the first cylindrical conductor 106. The surface indicated with the arrow 118 is the contact surface 118 for the second brush to contact the conductive elements 112. In this example the various layers and components are not drawn to scale. The contact surfaces 116 and 118 in this drawing are not drawn at the same level. For this particular embodiment the brushes may be adjusted to ride at different surfaces. However, it would be apparent to one skilled in the art that by adding more insulating layers it would be possible to have the surfaces 118 and 116 to be coplanar or approximately coplanar. For instance the conductive elements 112 and the second cylindrical conductor could be at different levels instead of coplanar as they are shown in this Fig. For instance the second cylindrical conductor could be deeper within the cylindrical body 100. A via or wire or connections could then be used to connect the conductive elements 112 to the second cylindrical conductor 108.

Figure 2:
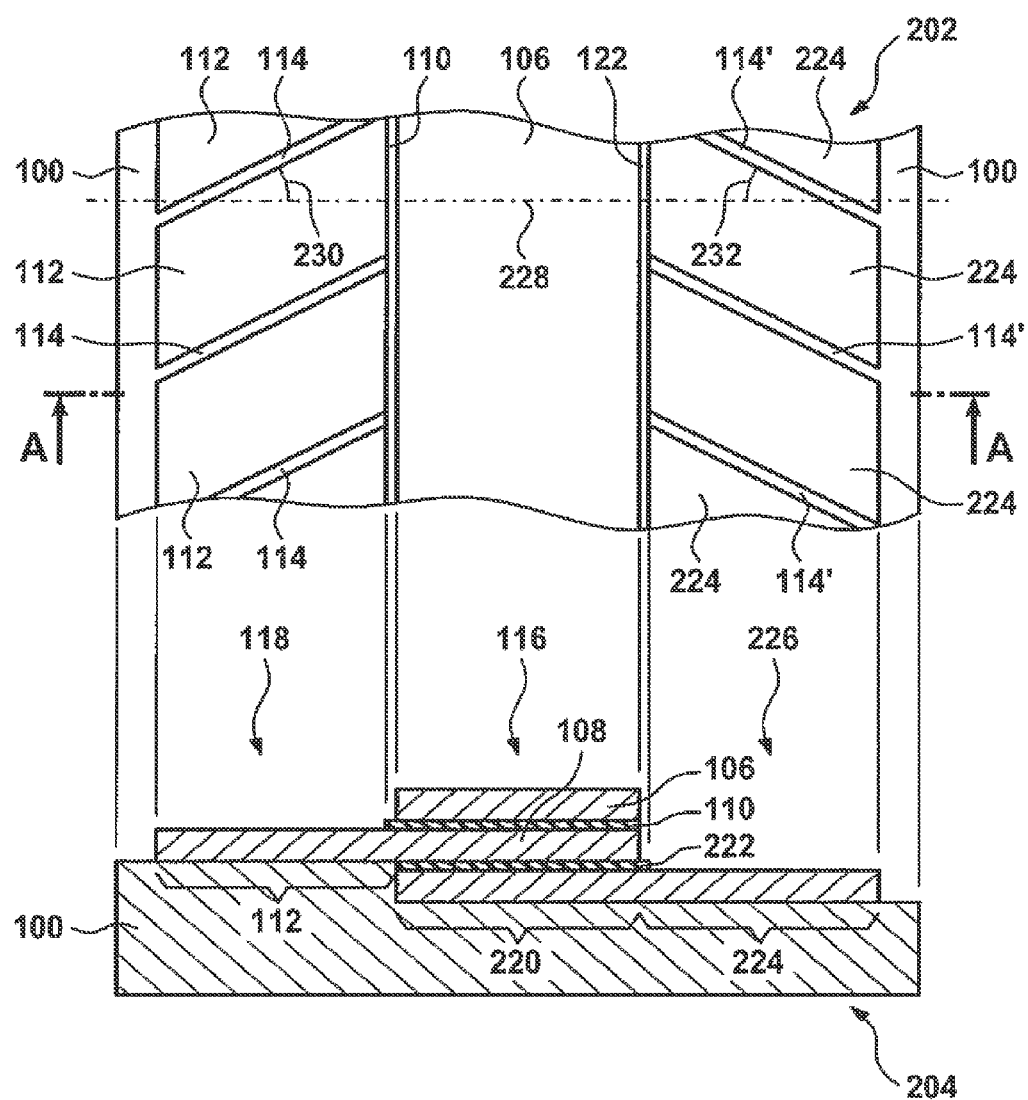
FIG. 2 shows a portion of a cylindrical body according to a further embodiment of the invention.

FIG. 2 shows a cylindrical body similar to that as shown in FIG. 1. Again there is a top view 202 and a sectional view 204 which is the section shown along the section lines labeled A-A. In the embodiment shown in FIG. 2 there is a third cylindrical conductor 220 which is below the second cylindrical conductor 108. There is an insulator 222 which electrically insulates the second cylindrical conductor 108 from the third cylindrical conductor 220. Again the third cylindrical conductor is connected to conductive elements 224. The conductive elements 224 form the second set of conductive elements. There is electrically isolating groove or gap 114' which electrically isolates the conductive elements 224 from each other. Again the third cylindrical conductor 220 and the conductive elements 224 are coplanar and are electrically connected (optionally made from a single piece of copper plate). The surface labeled 226 is the surface contact for the third brush. In this embodiment the surfaces 116, 118 and 226 are again at different levels. Again it is straight forward for one skilled in the art to have the surfaces 116, 118, 226 at the same level. For instance the second and third conductors 108, 220 could be embedded deeper into the cylindrical body 110. Vias or electrical connections or wires could then be used to connect the second cylindrical conductor 108 to the conductive elements 112 and the third cylindrical conductor 220 to the conductive elements 224.

A projection of the axis of symmetry 228 is also shown in view 202. The projection of the axis of symmetry 228 forms a first angle 230 with the grooves 114 and a second angle 232 with the grooves 114'.

Figure 3:
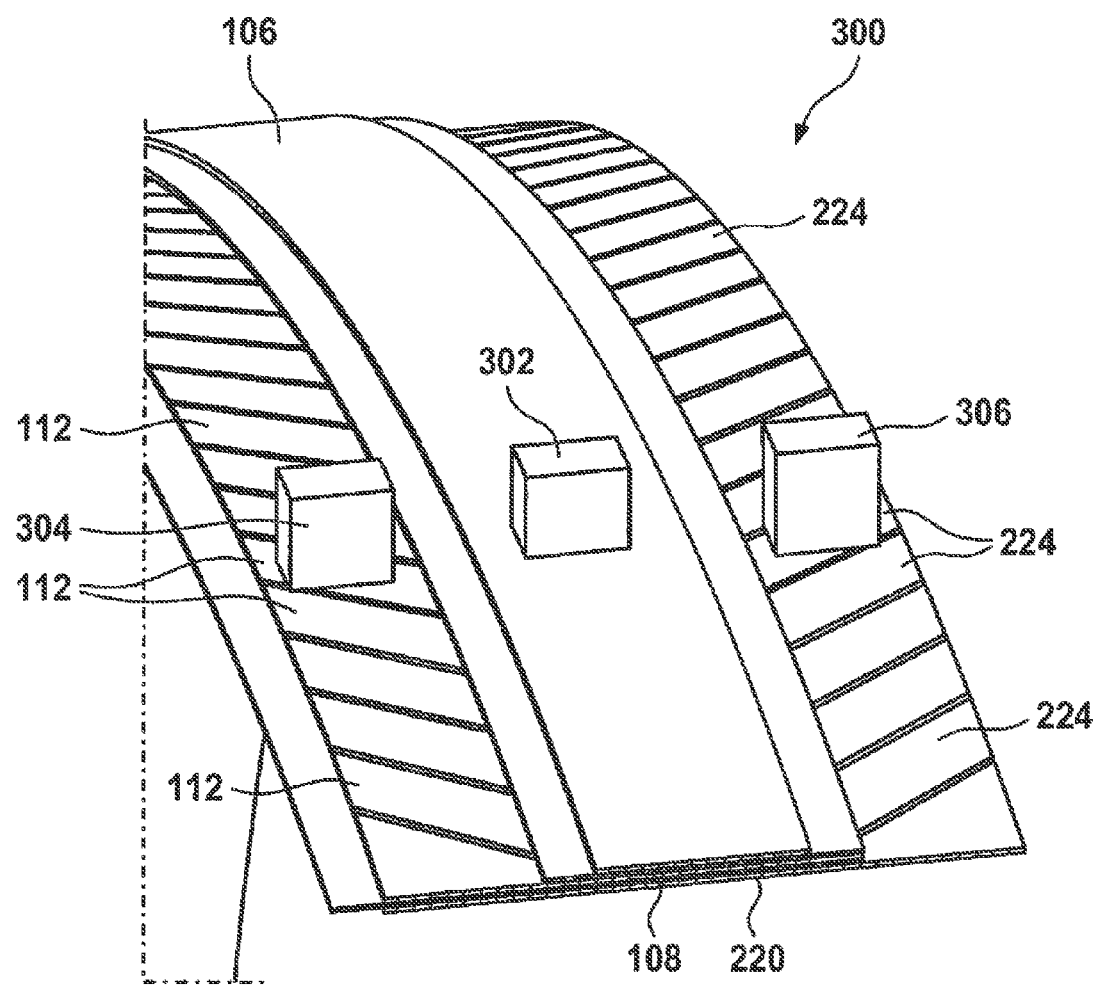
FIG. 3 shows a portion of a cylindrical body according to a further embodiment of the invention.

FIG. 3 shows a rendering of a portion of a cylindrical body 300. In this embodiment the first cylindrical conductor 106 is visible. There is a cut away section where the second cylindrical conductor 108 and the third cylindrical conductor 220 are visible. There are conductive elements 112 which form the first set of conductive elements and there are conductive elements 224 which form the second set of conductive elements. Not all of the first 112 and second 224 conductive elements are labeled. A first brush 302 can be seen to be in contact with the first cylindrical conductor 106. A second brush 304 can be seen to be in contact with several conductive elements 112 of the first set of conductive elements. There is a third brush 306 which is seen to be in contact with several conductive elements 224 of the second set of conductive elements. As either the cylindrical body 300 or the brushes 302, 304, 306 rotate only a portion of the first conductive elements are in contact with the second brush 304 and a portion of the conductive elements 224 are in contact with the third brush 306. It can be seen that the electric current will not be conducted by the first set of conductive elements 112 or the second set of conductive elements 224 around the circumference of the cylindrical body 300. The current will be conducted to the second cylindrical conductor 108 and the third cylindrical conductor 220. The current will then be conducted circumferentially around these cylindrical conductors 108, 220.

In a practical embodiment, the conductive elements 112 and 224 of the second and third cylindrical conductors are formed as flanges. Contact then can be made with the first (outermost) conductor 106 via a first brush 302 that makes contact with the outer radial face of the first conductor 106. To allow for contact with the second and third conductors 108, 220, each has an outer flange section 112, 224 (respectively) that extends outwardly, one in each longitudinal direction. Thus, the flange section 112 of the second conductor 108 extends longitudinally to the left in FIGS. 2 and 3, beyond the longitudinal extent of the first conductor 106 and also beyond the longitudinal extent of the third conductor 220. Likewise, the flange section 224 of the third conductor 220 extends longitudinally to the right in FIGS. 2 and 3, beyond the longitudinal extent of the first conductor 106 and also beyond the longitudinal extent of the second conductor 108.

This allows a second brush 304 to make contact with the second conductor 108 by sliding along its outer flange section 112, spaced longitudinally from the first conductor 106 and its associated first brush 302. Likewise, a third brush 306 can to make contact with the third conductor 220 by sliding along its outer flange section 224, also spaced longitudinally (albeit in the opposite direction) from the first conductor 106 and its associated first brush 302.

These flange sections create areas of the second and third conductors 108, 220 that are not aligned longitudinally with each other or with the first conductor 106. Thus, in order to confine the current carried by these conductors to the part of the conductor that is aligned longitudinally with the other conductors, each flange section 112, 224 has a pattern of regular electrical breaks such as slot 120. This is in the form of a narrow air gap cut or otherwise formed in the flange section 224, extending into the flange section so as to prevent circumferential current flow in the flange section. These may be at least a few millimeters wide, such as 2-4 mm wide, and may comprise air gaps or may be filled with an insulating material. The slot 120 can will ideally (as in this case) extend far enough in a longitudinal direction across the flange section so as to end at a point proximate to, aligned with, or beyond the longitudinal extent of the first conductor 106 thus narrowing the effective longitudinal conducting extent of the (respective) second or third conductor 108, 220 to one that is aligned with the first conductor 106.

A series of slots 120 are formed in each of the second and third conductors 108, 220. These may be spaced at 5-20° intervals around the conductors, such as the 10° interval illustrated. They can be arranged perpendicular to the edge of the conductor (as shown), or they may be angled (as shown) in one direction or the other in order to reduce wear on the brushes 304, 306 as they pass over the slots repeatedly. An angle of between 30° and 60° is preferred, such as 45°. Alternatively, filling the slots with a conductive material may also assist in reducing wear.

A treatment device or medical device such as a linear accelerator, for radiation therapy, may be mounted on a rotating structure located around an MRI scanner, thus enabling real-time magnetic resonance guided treatment. The electric power for the systems on the rotating structure can be supplied through a set of slip-rings, so as to allow continuous rotation of the therapy device.

Currents in the slip-rings may generate magnetic fields which will add to the static field in the imaging region of the scanner. If the currents are changing over time, the amplitude of these fields are preferably limited to less than about 50 nT in order to avoid severe ghosting artifacts in the magnetic resonance images. Conventional slip rings consisting of a set of discrete rings may generate too much magnetic field.

The stray-field of such currents may be minimized or reduced by reducing the area of the loops formed by the current paths in the slip ring. This may be achieved by manufacturing the slip ring as a sandwich from thin conductors with thin layers of insulation in between. The conducting layers are shaped in such a way that the transport currents in the ring (in azimuthal direction) are located directly on top of each other. This may be achieved by slits in the edges of the copper or conductive layers leaving only a through conducting path where the transport current is to flow. The slit edge regions of the conductors are partly exposed (by increasing the width of the conductors from layer to layer) and the brushes taking off the current are located on these exposed edge regions.

FIG. 3 shows an example of a slip ring with three conductors, as could be used in a three-phase AC current supply system. Any number of conductors is possible. The conductors are copper strips with a thickness of 0.5-3 mm. They are interspaced by thin insulating layers (for example G10) and may be bonded together. The exposed surfaces are used to contact the carbon brushes moving around the ring. By slitting the conductors everywhere except in the region directly underneath the topmost layer it is ensured that the transport current only flows there and the area of loops formed by currents in the ring is extremely small. Hence the stray field is very small, provided the sum of all conductors in the ring is zero. In order to ensure this condition, the ring is to be electrically interrupted at one location along the circumference. Orienting the slits at an angle reduces wear on the brushes as they move over the surface and also reduces sparks. The slip ring may be manufactured from a number of segments, for example each spanning 90 degrees.

Figure 4:
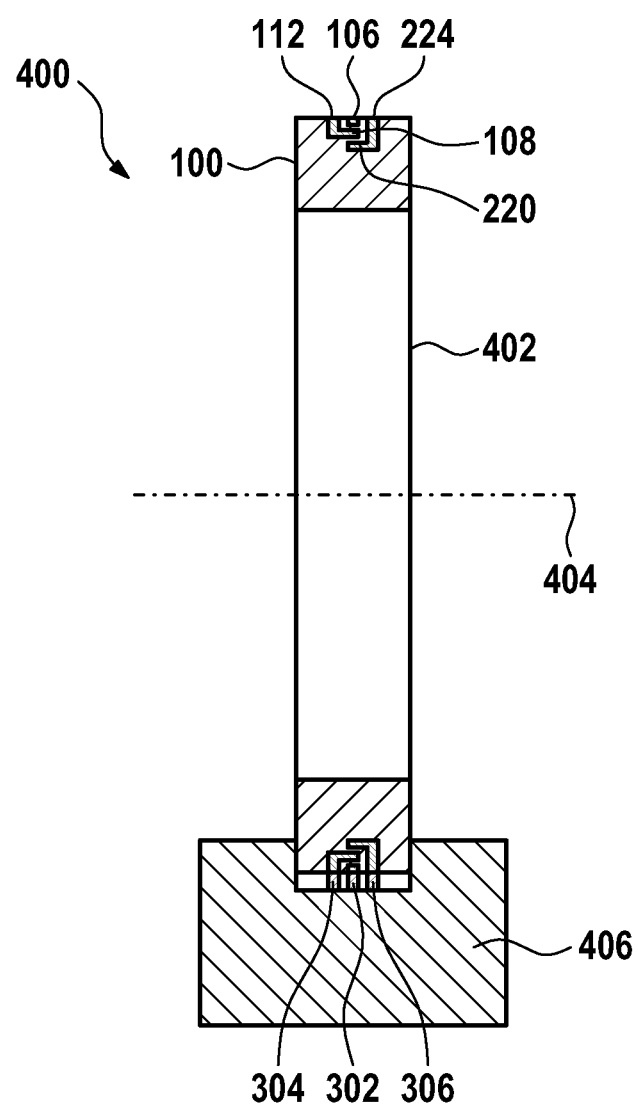
FIG. 4 shows a cross-sectional view of a slip ring assembly according to an embodiment of the invention.

FIG. 4 shows a cross-sectional view of a slip ring assembly according to an embodiment of the invention. The slip ring assembly 400 comprises a rotating member 402 adapted for rotating about an axis of symmetry 404. In this embodiment the cylindrical body 100 is integrated into the rotating member 402. The cylindrical body 100 can be seen to have a first cylindrical conductor 106, a second cylindrical conductor 108, and a third cylindrical conductor 220. All these conductors lie on a plane perpendicular to the axis of symmetry 404. The second cylindrical conductor 108 is connected to conductive elements 112. The third cylindrical conductor 220 is connected to conductive elements 224. The rotating member 402 is supported by a brush assembly 406. It is not shown in this diagram but the brush assembly 406 may have guides for guiding the rotating member 402 and/or a drive system for rotating the rotating member 402. For instance the rotating member 402 may have one or more tracks on its side that mate with several grooves on the brush assembly 406. The brush assembly 406 further comprises a first brush 302, a second brush 304, and a third brush 306. The first brush 302 contacts the first cylindrical conductor 106. The second brush 304 contacts the first set of conductive elements 112. The third brush 306 contacts the second set of conductive elements 224. In this embodiment the brushes 302, 304, 306 remain in a fixed position and the cylindrical body 100 is integrated into the rotating member 402.

Figure 5:
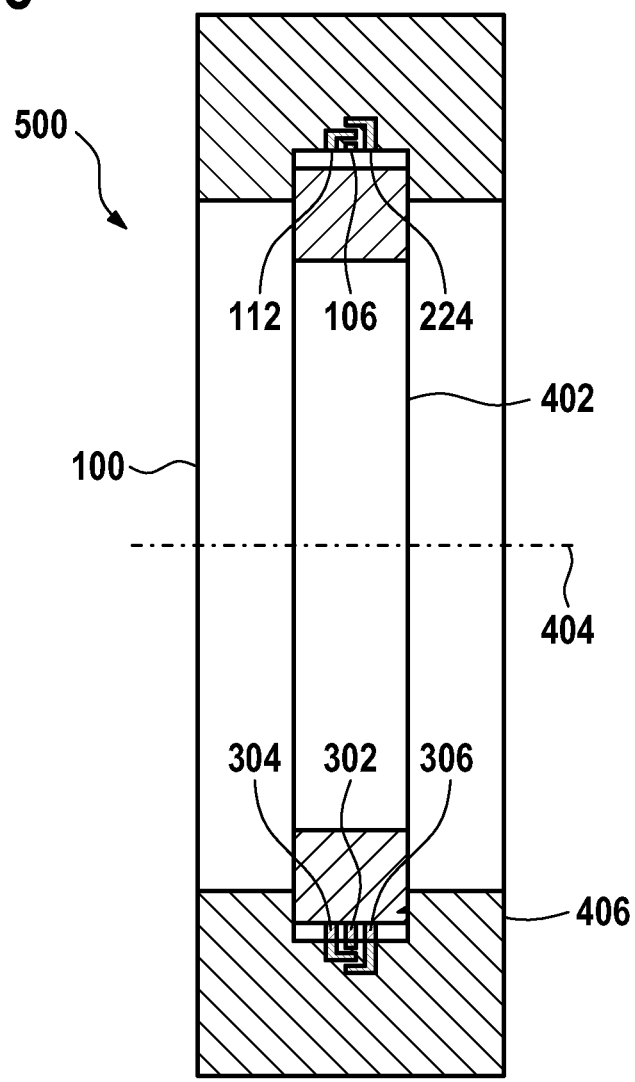
FIG. 5 shows a cross-sectional view of a slip ring assembly according to a further embodiment of the invention.

FIG. 5 shows an alternative embodiment of a slip ring assembly 500 according to an embodiment of the invention. The embodiment shown in FIG. 5 is similar to the embodiment shown in FIG. 4 except that in this embodiment the brush assembly 406 is integrated into the rotating member 402. The cylindrical body 100 in this embodiment is a cylinder which surrounds the rotating member 402. Some implementations of this embodiment may contain grooves or guides in the cylindrical body 100 for guiding the rotation of the rotational member 402. As the rotating member 402 rotates about the axis of symmetry 404 the brush assembly 406 rotates around to different positions and comes in contact with the first cylindrical conductor 106, the first set of conductive elements 112 and the second set of conductive elements 224.

Figure 6:
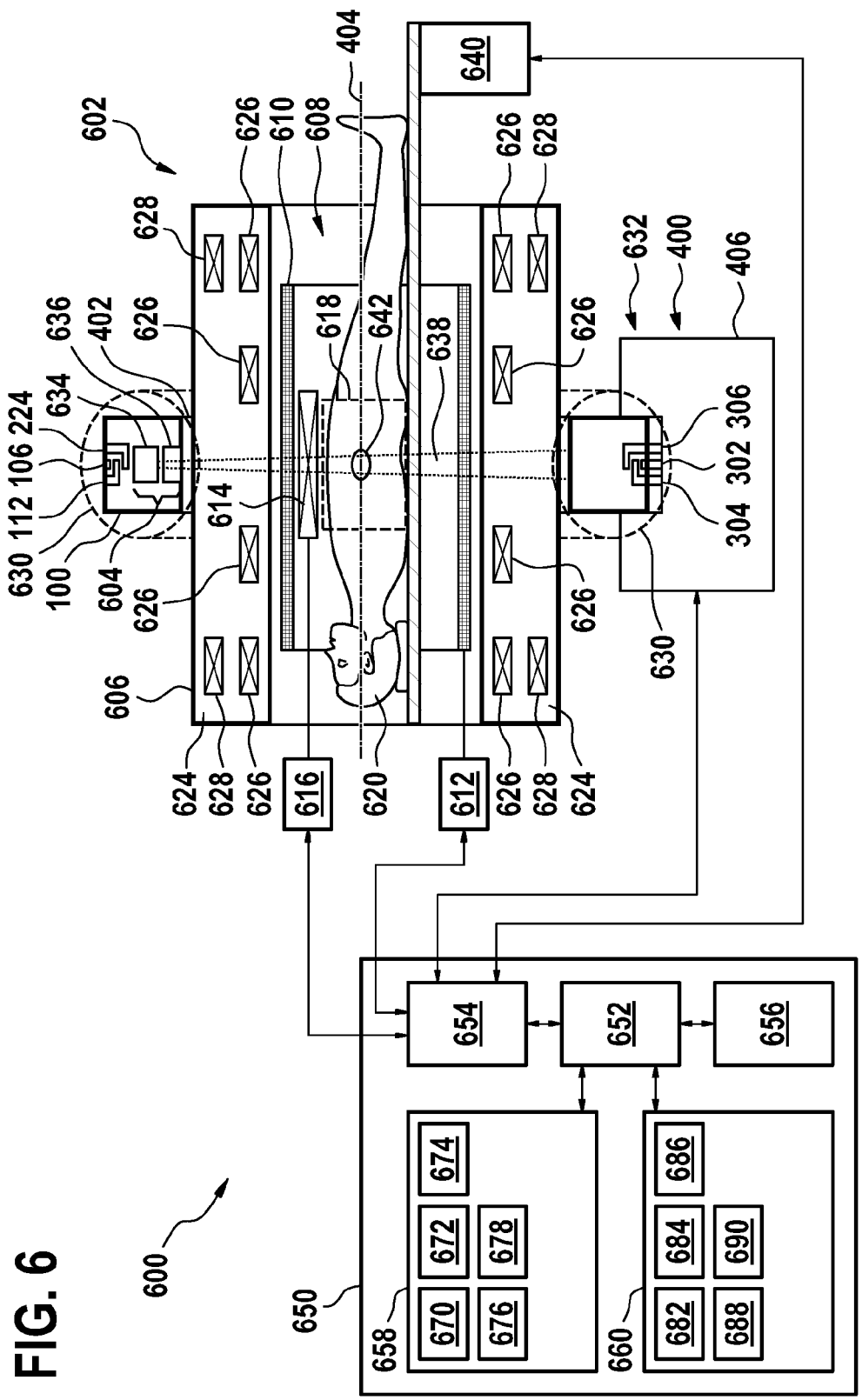
FIG. 6 illustrates a medical apparatus according to an embodiment of the invention.

FIG. 6 illustrates a medical apparatus 600 according to an embodiment of the invention. The medical apparatus 600 comprises a magnetic resonance imaging system 602. The magnetic resonance imaging system comprises a magnet 606. The magnet shown in FIG. 6 is a cylindrical type superconducting magnet. The magnet has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 608 of the cylindrical magnet 606 there is an imaging zone 618 where the magnetic field is strong and uniform enough to perform magnetic resonance imaging.

Within the bore 608 of the magnet there is also a magnetic field gradient coil 610 which is used to spatially encode magnetic spins within an imaging zone of the magnet during the acquisition of magnetic resonance data. The magnetic field gradient coil 610 is connected to a magnetic field gradient coil power supply 612. The magnetic field gradient coil is intended to be representative. Typically magnetic field gradient coils contain three separate sets of coils for spatially encoding in three orthogonal spatial directions. A magnetic field gradient power supply supplies current to the magnetic field gradient coils. The current supplied to the magnetic field coils is controlled as a function of time and may be ramped or pulsed.

Adjacent to the imaging zone 618 is a radio-frequency coil 614 which is connected to transceiver 616. Also within the bore 608 is a subject 620 reposing on a subject support 622. The radio-frequency coil 614 is adapted for manipulating the orientations of magnetic spins within the imaging zone and for receiving radio transmissions from spins also within the imaging zone. The radio-frequency coil 614 may contain multiple coil elements. The radio-frequency coil may also be referred to as a channel or an antenna. The radio-frequency coil 614 and radio frequency transceiver 616 may be replaced by separate transmit and receive coils and a separate transmitter and receiver. It is understood that the radio-frequency coil 614 and the radio frequency transceiver 616 are representative. The radio-frequency coil 614 may also represent a dedicated transmit antenna and a dedicated receive antenna. Likewise the transceiver may also represent a separate transmitter and receivers.

The medical apparatus shown in FIG. 6 includes a radiation therapy system 604. The magnet 606 is a superconducting magnet includes a cryostat 624 with several superconducting coils 626. There is also a compensation coil 628 which creates an area of reduced magnetic field 630 which surrounds the magnet 606. The radiation therapy system 604 in this embodiment is intended to be representative of radiation therapy systems in general. The components shown here are typical for LINAC and x-ray therapy systems. However with minor modifications such as using a split magnet charged particles or beta particle radiation therapy systems can also be illustrated using this diagram.

There is a gantry 632 which is used to rotate a radiotherapy source 334 about the magnet 606. The gantry comprises a slip ring assembly 400 equivalent to the slip ring assembly shown in FIG. 4. The gantry 632 is rotated about the axis of symmetry 404 by the brush assembly 406. There is a radiation therapy source 634 which is rotated by the rotational member 402. The radiotherapy source 634 generates a radiation beam 638 which passes through collimator 636. In the Fig. a target zone is labeled 642 which is irradiated by the radiation beam 638 is shown. As the radiation source 634 rotates about the axis of symmetry 404 the target zone 642 is irradiated. There is also a support positioning system 640 for positioning the support 622 to optimize the location of the target zone 642 relative to the radiation therapy system 604. The magnet 606 or the magnetic field generated by the magnet 606 may also have an axis of symmetry. The axis of symmetry of the magnet or magnetic field may in some embodiments be identical with the axis of symmetry 404 of the rotating member 402.

The medical apparatus 600 is further shown as comprising a computer system 650. The computer system comprises a processor 652, a hardware interface 654, a user interface 656, computer storage 658, and computer memory 660. The processor 652 is connected to and can operate with all of these components 654, 656, 658, 660. The hardware interface 654 is shown as being connected to the transceiver 616, the power supply 612, the brush assembly 406, and the support positioning system 640. The hardware interface 654 allows the processor 652 to send and receive control signals to all of these components 406, 612, 616, 640.

The computer storage 658 is shown as containing magnetic resonance data 670 that was acquired using the magnetic resonance imaging system 602. The computer storage 658 is further shown as containing the magnetic resonance image 672 that was reconstructed from the magnetic resonance data 670. The computer storage 658 is further shown as containing a treatment plan 674. The treatment plan contains instructions executable by the medical apparatus 600 which case the medical apparatus to treat the subject 620 using the radiotherapy source 634. The computer storage 658 is further shown as containing an image registration 676. The image registration allows the processor 652 to locate the target zone 642 within the subject 620. The computer storage 658 further contains at least one pulse sequence 678. The pulse sequence 678 may be used for acquiring data for guiding the radiotherapy source 634 and/or for acquiring magnetic field measurements from a phantom which is not shown in this diagram.

The computer memory 660 is shown as containing computer executable code for controlling the operation and function of the medical apparatus 600. The computer storage is shown as containing a control module 682. The control module contains the instructions for operating and controlling the medical apparatus 600. The control module may for instance contain code which uses sensor data from the gantry 632 to determine the angular position of the rotating member 402. The control module may for example issue commands to halt acquisition of magnetic resonance data when the gantry is in such a position that the rotating member is within a predetermined angular range of a predetermined rotational angle. the predetermined rotational angle may define a position where at least one of the first cylindrical conductor and the second cylindrical conductor comprises an electrically isolating break.

The computer memory 660 is further shown as containing a command generation module 684. The command generation module 684 is adapted for using the treatment plan 674 and in some embodiments the image registration 676 to generate commands which cause the medical apparatus 600 to treat the target zone 642. The computer memory 660 is shown as further containing a magnetic resonance control module 686. The magnetic resonance control module 686 is adapted for generating commands and controlling the operation of the magnetic resonance imaging system 602 using a pulse sequence 678. The computer memory 660 is further shown as containing an image reconstruction module 688. The image reconstruction module 688 contains computer executable code for reconstructing the magnetic resonance image 672 from the magnetic resonance data 670. The computer memory 660 is further shown as containing an image segmentation module 690. The image segmentation module 690 contains computer executable code for segmenting the magnetic resonance image 672 and performing the image registration 676.

The embodiment in FIG. 6 is exemplary. The radiation therapy system 604 may be replaced with a different type of medical device. It may be for example, but not limited to: an X-ray machine, a linear accelerator, charged particle beam optics, and a computed tomography, system.

FIG. 7 shows a cylindrical body similar to that as shown in FIG. 1. Again there is a top view 702 and a sectional view 704 which is the section shown along the section lines labeled A-A. Below the first cylindrical conductor 106 is the second cylindrical conductor 108. There is an insulating layer 110 separating the first cylindrical conductor 106 from the second cylindrical conductor 108. Looking at the top view to the left of the first cylindrical conductor are several conductive elements 712. The conductive elements 712 are the first set of conductive elements. The conductive elements 712 are formed by a groove 714 that is cut into the second cylindrical conductor 108.

The surface marked 116 is the surface along which the first brush would contact the first cylindrical conductor 106. The surface indicated with the arrow 118 is the contact surface 118 for the second brush to contact the conductive elements 112. In this example the various layers and components are not drawn to scale. The first cylindrical conductor 106, the insulating layer 110, and the second cylindrical conductor 108 are shown in a cut away view in the top view 702 so that the single piece construction of the second cylindrical conductor 108 and the conductive elements 712 is visible.

The contact surfaces 116 and 118 in this drawing are not drawn at the same level. For this particular embodiment the brushes may be adjusted to ride at different surfaces. However, it would be apparent to one skilled in the art that by adding more insulating layers it would be possible to have the surfaces 118 and 116 to be coplanar or approximately coplanar. For instance the conductive elements 112 and the second cylindrical conductor could be at different levels instead of coplanar as they are shown in this Fig. For instance the second cylindrical conductor 108 could have a bend in it which allows the surface 118 and 116 to be at the same level.

The embodiment shown in FIG. 2 could also be constructed in a manner equivalent to the embodiment shown in FIG. 7. The conductive elements 112 and 224 could both be formed by grooves cut into the cylindrical conductors 108 and 220. Likewise the surfaces 118, 116, and 226 could also be made co-planar by bends in the cylindrical conductors 108 and 220.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A slip ring assembly comprising:
a cylindrical body with an axis of symmetry;
a rotating member for rotating about the axis of symmetry,
a first cylindrical conductor, wherein the first cylindrical conductor is attached to the cylindrical body;
a second cylindrical conductor, wherein the first and second cylindrical conductors overlap at least partially, wherein the second cylindrical conductor is connected to the cylindrical body, wherein the first cylindrical conductor and the second cylindrical conductor are electrically isolated;
a set of conductive elements, wherein each of the set of conductive elements is connected to the second cylindrical conductor, wherein a first set of conductive elements is formed by the first cylindrical contact and the first cylindrical contact is separated into the set of conductive elements by electrically isolating grooves; and
a brush assembly comprising a first brush and a second brush, wherein the first brush is configured to contact the first cylindrical conductor when the rotating member rotates about the axis of symmetry, wherein the second brush is configured to contact the set of conductive elements when the rotating member rotates about the axis of symmetry.

2. The slip ring assembly of claim 1, wherein the slip ring assembly further comprises at least one additional cylindrical conductor, wherein the first cylindrical conductive element and the at least one additional cylindrical conductor overlap at least partially, wherein the at least one additional cylindrical conductor is connected to the cylindrical body, wherein the at least one additional cylindrical conductor and the first cylindrical conductor are electrically isolated, wherein the slip ring assembly further comprises at least one additional set of conductive elements, wherein each of the at least one additional set of conductive elements is connected to the at least one additional cylindrical conductor, wherein the brush assembly comprises at least one additional brush, wherein the at least one additional brush is operable to contact the at least one additional set of conductive elements when the rotating member rotates about the axis of symmetry.

3. The slip ring assembly of claim 1, wherein the rotating member comprises the brush assembly.

4. The slip ring assembly of claim 1, wherein the rotating member comprises the cylindrical body.

5. A medical apparatus comprising:
a magnetic resonance imaging system for acquiring magnetic resonance data, wherein the magnetic resonance imaging system comprises a magnet;
a medical device; and
a slip ring assembly operable for supplying electrical power to the medical device; wherein the slip ring assembly comprises:
a cylindrical body with an axis of symmetry,
a rotating member for rotating about the axis of symmetry and for rotating about the magnet, wherein the medical device is mounted to the rotating member;
a first cylindrical conductor, wherein the first cylindrical conductor is attached to the cylindrical body;

a second cylindrical conductor, wherein a first and a second cylindrical conductive elements overlap at least partially, wherein the second cylindrical conductor is connected to the cylindrical body, wherein the first cylindrical conductor and the second cylindrical conductors are electrically isolated;

a first set of conductive elements, wherein each of the set of conductive elements is connected to the second cylindrical conductor, wherein the first set of conductive elements is formed by a first cylindrical contact, wherein the first cylindrical contact is separated into the set of conductive elements by electrically isolating grooves; and a brush assembly comprising a first brush and a second brush, wherein the first brush is operable to contact the first cylindrical conductor when the rotating member rotates about the axis of symmetry, wherein the second brush is operable to contact the set of conductive elements when the rotating member rotates about the axis of symmetry.

6. The medical apparatus of claim 5, wherein the electrically isolating grooves are formed at a predetermined angle with respect to a projection of the axis of symmetry onto the first cylindrical contact.

7. The medical apparatus of claim 6, wherein the isolating grooves form a fishbone pattern.

8. The medical apparatus of claim 5, wherein at least one of the first cylindrical conductor and the second cylindrical conductor comprises an electrically isolating break at a predetermined rotational angle of the rotating member.

9. The medical apparatus of claim 8, wherein the medical apparatus comprises a control system adapted to halt the acquisition of magnetic resonance data by the magnetic resonance imaging system when the rotating member is within a predetermined angular range of the predetermined rotational angle.

10. The medical apparatus of claim 5, wherein the rotating member comprises the brush assembly.

11. The medical apparatus of claim 5, wherein the rotating member comprises the cylindrical body.

12. The medical apparatus of claim 5, wherein the medical apparatus further comprises:

a third cylindrical conductor, wherein the first cylindrical conductor and the third cylindrical conductor overlap at least partially, wherein the third cylindrical conductor is connected to the cylindrical body, wherein the third cylindrical conductor and the second cylindrical conductor are electrically isolated, wherein the third cylindrical conductor and the first cylindrical conductor are electrically isolated;

a second set of conductive elements, wherein each of the set of conductive elements is connected to the third cylindrical conductor, wherein the brush assembly comprises a third brush, wherein the third brush is operable to contact the second set of conductive elements when the rotating member rotates about the axis of symmetry, wherein the second set of conductive elements is formed by a second cylindrical contact, wherein the second cylindrical contact is separated into the set of conductive elements by second electrically isolating grooves, wherein the second electrically isolating grooves are formed at a predetermined angle with respect to a projection of the axis of symmetry onto the second cylindrical contact.

13. The medical apparatus of claim 5, wherein the medical device is any one of the following: a X-ray machine, a linear accelerator, charged particle beam optics, and a computed tomography system.

* * * * *